United States Patent
Sawyer et al.

(10) Patent No.: US 10,226,043 B2
(45) Date of Patent: *Mar. 12, 2019

(54) CONTROLLED RELEASE BIOCIDAL SALTS

(71) Applicant: Nevada Naturals Inc., Albuquerque, NM (US)

(72) Inventors: Anthony J. Sawyer, Albuquerque, NM (US); Richard F. Stockel, Bridgewater, NJ (US)

(73) Assignee: NEVADA NATURALS INC., Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/000,412

(22) Filed: Jan. 19, 2016

(65) Prior Publication Data

US 2016/0128328 A1     May 12, 2016

Related U.S. Application Data

(63) Continuation of application No. 14/176,597, filed on Feb. 10, 2014, now Pat. No. 9,271,495, which is a continuation of application No. 12/658,200, filed on Feb. 4, 2010, now abandoned, which is a continuation-in-part of application No. 12/586,695, filed on Dec. 22, 2009, now abandoned, and a continuation-in-part of application No. 12/589,155, filed on Oct. 19, 2009, now abandoned, which is a continuation-in-part of application No. 12/583,919, filed on Aug. 27, 2009, now abandoned, and a continuation-in-part of application No. 12/455,197, filed on May 28, 2009, now Pat. No. 8,193,244, which is a continuation-in-part of application No. 11/633,231, filed on Dec. 4, 2006, now abandoned.

(60) Provisional application No. 61/196,455, filed on Oct. 17, 2008, provisional application No. 60/748,719, filed on Dec. 9, 2005.

(51) Int. Cl.

| | |
|---|---|
| *A01N 37/00* | (2006.01) |
| *A61K 31/215* | (2006.01) |
| *A01N 37/12* | (2006.01) |
| *A01N 37/44* | (2006.01) |
| *A61K 31/24* | (2006.01) |
| *A01N 25/00* | (2006.01) |
| *A01N 47/44* | (2006.01) |
| *A23L 3/3463* | (2006.01) |
| *A23L 3/3526* | (2006.01) |
| *B65D 81/28* | (2006.01) |
| *A23L 3/3508* | (2006.01) |
| *A23B 4/20* | (2006.01) |
| *A01N 43/38* | (2006.01) |
| *A01N 43/50* | (2006.01) |

(52) U.S. Cl.
CPC ............. *A01N 37/44* (2013.01); *A01N 43/38* (2013.01); *A01N 43/50* (2013.01); *A01N 47/44* (2013.01); *A23B 4/20* (2013.01); *A23L 3/34635* (2013.01); *A23L 3/3508* (2013.01); *A23L 3/3526* (2013.01); *B65D 81/28* (2013.01); *A23V 2002/00* (2013.01); *Y10T 428/662* (2015.04); *Y10T 442/2525* (2015.04)

(58) Field of Classification Search
None
See application file for complete search history.

(56) References Cited

U.S. PATENT DOCUMENTS

| | | | |
|---|---|---|---|
| 3,825,560 | A | 7/1974 | Saito et al. |
| 3,947,589 | A | 3/1976 | Misato et al. |
| 5,780,658 | A | 7/1998 | Martinez-Pardo et al. |
| 7,074,447 | B2 | 7/2006 | Bonaventura et al. |
| 7,074,459 | B2 | 7/2006 | Stockel |
| 7,407,679 | B2 | 8/2008 | Beltran et al. |
| 2004/0166082 | A1 | 8/2004 | Urgell-Beltran et al. |
| 2004/0265443 | A1 | 12/2004 | Beltran et al. |

FOREIGN PATENT DOCUMENTS

| | | | | |
|---|---|---|---|---|
| WO | WO9944444 A1 | 9/1999 | | |
| WO | WO 2005000253 A1 | * | 1/2005 | ............... A61K 8/25 |

OTHER PUBLICATIONS

International Search Report and Written Opinion of the International Searching Authority dated Oct. 27, 2010 for corresponding International Application No. PCT/US2010/000607.
Infante, M. Rosa et al., "Non-Conventional Surfactants from Amino Acids and Glycolipids: Structure, Preparation and Properties", Colloids and Surfaces A: Physiochemical and Engineering Aspects 123-124 (1997) pp. 49-70.

* cited by examiner

*Primary Examiner* — Layla Soroush
(74) *Attorney, Agent, or Firm* — Benesch, Friedlander, Coplan & Aronoff LLP

(57) ABSTRACT

A controlled release biocidal salt of a first component comprises a cation of a $N^\alpha$-($C_1$-$C_{22}$) alkanoyl di-basic amino acid alkyl ($C_1$-$C_{22}$) ester cationic biocidal molecule and a second component comprising an anion of a monomeric anionic molecule having insignificant biocidal activity. The salt is characterized such that when the salt is exposed to an aqueous medium, the salt partially dissolves thereby releasing biocidal ions in an amount sufficient to exceed the MIC or MBC of a target bacteria being controlled, and further characterized as leaving a residual reservoir of undissolved salt capable of releasing more biocidal ions as the salt is consumed or otherwise removed from the environment encompassing the target bacteria. The preferred cationic biocidal molecule comprises $N^\alpha$-lauroyl-L-arginine ethyl ester ("LAE").

5 Claims, No Drawings

CONTROLLED RELEASE BIOCIDAL SALTS

REFERENCE TO RELATED APPLICATIONS

This application is a continuation of application Ser. No. 14/176,597, filed Feb. 10, 2014, which is a continuation of application Ser. No. 12/658,200, filed Feb. 4, 2010, which is a continuation-in-part of application Ser. No. 12/589,155, filed Oct. 19, 2009, now abandoned, (claiming the benefit of provisional application Ser. No. 61/196,455, filed Oct. 17, 2008), which is a continuation-in-part of application Ser. No. 12/583,919 filed Aug. 27, 2009, now abandoned, as well as a continuation-in-part of application Ser. No. 12/455,197 filed May 28, 2009 (now U.S. Pat. No. 8,193,244), and which is a continuation-in-part of application Ser. No. 11/633,231 filed Dec. 4, 2006, now abandoned, (claiming the benefit of provisional application Ser. No. 60/748,719 filed Dec. 9, 2005), and which is a continuation-in-part of application Ser. No. 12/586,695 filed Dec. 22, 2009, now abandoned. The disclosures of all of the foregoing applications are incorporated by reference herein in their entirety.

FIELD OF THE INVENTION

The invention relates to controlled release biocidal salts that are environmentally safe that can have antimicrobial, antibacterial, antiviral, antifungal properties and/or skin/hair activity. The salts of the invention which can be used as preservatives comprise two components: a first component comprising a cation of a $N^\alpha$-($C_1$-$C_{22}$) alkanoyl di-basic amino acid alkyl ($C_1$-$C_{22}$) ester cationic biocidal molecule and a second component comprising an anion of a monomeric anionic molecule having insignificant biocidal activity.

BACKGROUND OF THE INVENTION

The use of environmentally beneficial compositions, especially those that are referred to as "green", is important in choosing biocidal materials that have controlled release (also referred to as extended release) properties and also can be used as preservatives. The use of natural or naturally-derived materials is also very much of interest in topically applied and ingested compositions. It is also important that both green and naturally-derived materials be utilized in a composition that will provide antimicrobial, antibacterial, antifungal, antiviral and skin/hair beneficial properties as well as preservative capability and controlled release properties. If all of the components of a biocidal composition are GRAS
(Generally Regarded as Safe) and are approved for food use, the resulting composition could also be ingested with little or no side effects. Since the use of food-grade materials are being promoted as a strategy of selecting ingredients that are intended to be applied to skin/hair, compositions utilizing GRAS ingredients would meet such need.

Many presently-used preservatives are not green and are not natural or naturally-derived and many are not approved for food use. There is a growing movement in the cosmetics industry to avoid the use of ingredients that cannot be eaten. Furthermore, commonly-used preservatives do not possess controlled release properties which would allow continuous release of the preservative at effective levels as the preservative is consumed. If a preservative composition having controlled release properties also included GRAS ingredients that have an antimicrobial component as well as a naturally occurring component that has skin/hair benefits, then such approach would be beneficial in reducing the potential irritation from hash chemicals while improving skin/hair health.

OBJECTS OF THE INVENTION

It is an object of the invention to provide controlled release biocidal salts that are environmentally safe that can have antimicrobial, antibacterial, antiviral, antifungal properties and/or skin/hair activity.

It is an additional object of the invention to provide methods for the preservation of food products that utilize GRAS materials such that the materials will be lethal to the microorganisms found in such food products.

It is a further object of the invention to provide methods for the preservation of food products involving the use of salts of GRAS materials that will not only be safe and efficacious, but also have a long-lasting lethality to microorganisms found in such food products.

The foregoing objects and other objects of the invention will be apparent from the details of the invention set forth below.

SUMMARY OF THE INVENTION

The invention pertains to environmentally safe controlled release biocidal salts that have antimicrobial, antibacterial, antifungal and antiviral properties as well as skin/hair beneficial properties. Such salts can be considered to be green and natural or naturally derived and are particularly useful for cosmetic applications and for the preservation of foods.

DETAILS OF THE INVENTION

The controlled release biocidal salts of the invention comprise a first component comprising a cation of a $N^\alpha$-($C_1$-$C_{22}$) alkanoyl di-basic amino acid alkyl ($C_1$-$C_{22}$) ester cationic biocidal molecule and a second component comprising an anion of a monomeric anionic molecule having insignificant biocidal activity. The salt is such that when it is exposed to an aqueous medium, the salt partially dissolves thereby releasing biocidal ions in an amount sufficient to exceed the MIC or MBC of a target bacteria being controlled, and further characterized as leaving a residual reservoir of undissolved salt capable of releasing more biocidal ions as the salt is consumed or otherwise removed from the environment encompassing the target bacteria.

Preferably, the di-basic amino acid of the first component is selected from the group consisting of arginine, lysine, histidine and tryptophan. The most preferred cationic biocidal molecule is $N^\alpha$-lauroyl-L-arginine ethyl ester, hereinafter frequently referred to as "LAE".

The terms "MIC" and "MBC" employed in the description and the claims, refer to the Minimum Inhibitory Concentration and Minimum Bactericidal Concentration, respectively.

Typically, about 2 to about 500 ppm of biocidal ions are released when the salt is exposed to an aqueous medium such as water. This can be quite ample for many bactericidal applications. For example, about 2-128 ppm of LAE biocidal ions, about 2-8 ppm of chlorhexidine ("CHX") biocidal ions, about 1-8 ppm of cetyl pyridinium chloride ("CPC"), about 100-400 ppm of para-chloro-meta-xylenol ("PCMX") and about 2-40 ppm of triclosan biocidal ions are needed to inhibit or kill microbes such as bacteria, fungi and yeasts. However, this will vary with the antibacterial activity of the selected biocidal ion. Microbiological testing can be used to establish the MIC or MBC of a target microbe. Simple analyses can be used to determine the solubility of the biocidal salt and hence to establish its ability to provide continuous release as the biocidal ion is consumed or is otherwise removed from the environment encompassing the target microbe.

For those situations in which a very rapid inhibition or kill of a microbe is required, excess amounts of the first component can be provided together with the polymeric biocidal salt to rapidly sanitize the area to be treated.

In general, the molar ratio of the first component to the second component Is such that there is an equivalency between the first component and the second component. For those situations in which a very rapid inhibition or kill of a microbe is required, excess amounts of the first component can be provided together with the salt of the invention to rapidly sanitize the area to be treated. Typically, the salt of the invention releases at least about 2 ppm of biocidal ions when the salt is exposed to an aqueous medium such as water.

Preferably, the monomeric anionic molecule having insignificant biocidal activity will contain a moiety selected from the group consisting of carboxylic, hydroxycarboxylic, phenolic (e.g., resorcinol, ferulic acid), pentacyclic triterpenoid, enol (e.g., ascorbic acid, its esters and its phosphate salts and dehydroacetic acid), acidic amino acid, a protein having a residual negative charge, a phosphate moiety present on a DNA nucleotide, an anionic phospho-lipid, bis-phosphonate, phosphonate, sulfate, sulfonate and mixtures of the foregoing moieties.

Preferably, the carboxylic moiety comprises a carboxylic acid selected from the group consisting of adapalene; isotretinoin; pantothenic acid; benzoic acid; salicyclic acid; retinoic acid; tretinoin; an aldobionic acid; undecylenic acid; an α-hydroxycarboxylic acid; a β-hydroxycarboxylic acid; an α-ketocarboxylic acid; a β-keto carboxylic acid; an aromatic carboxylic acid; and azelaic acid. Suitable α-hydroxycarboxylic acids include glycolic, lactic, tartaric, mandelic, malic, citric, gluconic, glyceric and glyoxylic.

Alternatively, the carboxylic moiety may be a $C_8$-$C_{22}$ saturated or un-saturated fatty acid. Suitable examples of such saturated fatty acids include lauric, myristic, palmitic, and stearic acids. Suitable examples of such unsaturated fatty acids include linolenic, arachidonic, oleic, linoleic, eicosapentanoic and docosahexenoic acids.

Other compounds useful as the second component are the polyphenols and derivatives thereof. Polyphenols are a group of chemical substances found in plants and are characterized by the presence of one or more phenolic units. Examples of suitable polyphenols are ferulic acid, reservatrol, gallic acid, coumaric acid, catechin, caffeic acid, vanillic acid, chlorogenic acid, aplanin and sinapyl arbutin. Additional useful second components are the pentacyclic triperpenoids, such as betulinic acid, moronic acid, ursolic acid and oleanolic acid.

For many applications, it is desirable that the salts of the invention include a saturated $C_6$-$C_{14}$ fatty acid monoglyceride such as glycerol monolaurate. If present, the monolaurate is utilized in an amount of about 1 to about 10 wt. %, based on the weight of the salt.

The salts of the invention may be prepared by a metathesis reaction between an acid salt of the first component and an alkali or alkaline earth metal salt of the second component. Alternatively, the salts of the invention may be prepared by an acid-base reaction between the first component present in the form of its free base and the second component present in the form of an undissociated molecule having a transferable proton. The metathesis and acid-base reactions are described in detail below.

The Metathesis Reaction

As noted in the *McGraw-Hill Dictionary of Scientific and Technical Terms* (5$^{th}$ Edition, 1994), metathesis is a reaction involving the exchange of elements or groups as in the general reaction:

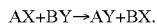

AX+BY→AY+BX.

The metathesis reaction is straight forward and can be readily carried out in aqueous solutions using water alone or a mixture of water and up to about 85 wt. % of a solvent such as a $C_1$-$C_4$ alcohol, e.g., methanol, ethanol, isopropanol, n-butanol, etc. Typically the water alone or water-alcohol solvent will be utilized in an amount of about 40 to about 85 wt. %, based on the weight of the reaction mixture. Water is the solvent of choice; the by-products are harmless salts and the yields of the salt of the invention range from excellent to quantitative. Where one or both of the reactants are only slightly soluble in water, alcohols or other solvents can be used to carry out the reaction.

An alkali or alkaline earth metal (e.g., Na, K, Li, Ca, etc.) salt of the selected first component is formed by reacting it with an equivalent amount of an alkali or alkaline earth metal hydroxide in water or water-alcohol solution. An acid salt, e.g., acetate, hydrohalide, gluconate, sulfate, etc. of the selected second component is formed by reacting it with an equivalent amount of an acid such as acetic, hydrochloric, hydrobromic, gluconic acid, sulfuric, etc. in water or water-alcohol solution. Thereafter, an equivalent amount of the aqueous alkali or alkaline earth metal salt solution of the selected first component is mixed with the aqueous acid salt solution of the selected second component. The concentration of the reactants can vary from about 20 to about 60 wt. % of the total reaction mixture. Mixing is continued at room temperature for several minutes up to about one hour. The reaction product may be readily recovered by decantation of the supernatant layer (which contains the byproduct salts) or by filtration. The solid layer consisting of the salt of the invention may be used as is for many of the applications recited below or dried (e.g., in air, in vacuuo at a temperature of about 50 to about 130° C., etc.). If desired, the salt may be recrystallized using a solvent such that the solubility of the salt in the solvent is low at room temperature, but the solubility increases significantly near the boiling point of the solvent. The $K_{sp}$ of the salt of the invention will generally be about $6 \times 10^{-2}$ moles/liter or less.

The Acid-Base Reaction

It is preferred to use the acid-base reaction to prepare the polymeric salts of the invention rather than the metathesis reaction since the acid-base reaction does not result in by-product salts that must be disposed of in an environmentally sound manner. However, in order to prepare the salts of the invention by an acid-base reaction, it is necessary that the selected first component be present in the form of its free base having a p$K_b$ numerical value of at least about 6 and the second component be present in the form of its undissociated acid having a p$K_a$ numerical value of about 8 or less. Alternatively, the selected first component must be present in the form of its acid having a p$K_a$ numerical value of about 8 or less and the second component must be present in the form of its free base having a $pK_b$ numerical value of at least about 6.

The acid-base reaction is typically carried out in the presence of about 40 to about 80 wt. % of a solvent consisting of a $C_1$-$C_4$ alcohol or a mixture of about 20 to about 60 wt. % water and such alcohol. The reaction mixture is generally stirred under reflux for about 30 minutes to about 10 hours and the reaction product, i.e., the polymeric biocidal salt of the invention, is recovered by evaporation of the solvent. If desired, the reaction product may be recrystallized using a solvent or a mixture of solvents such as isopropanol, propylene glycol, dimethyl formamide, etc., or with small amounts of water.

As in the case of the metathesis reaction, the molar ratio of the first component to the second component is such that the polymeric biocidal salt of the invention will bear a charge ranging from less than 50% negative charge to neutrality to less than 50% positive charge.

The acid-base reaction may be illustrated by the following equation:

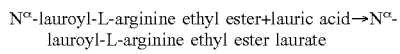
$N^\alpha$-lauroyl-L-arginine ethyl ester+lauric acid→$N^\alpha$-lauroyl-L-arginine ethyl ester laurate

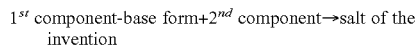
$1^{st}$ component-base form+$2^{nd}$ component→salt of the invention

Formation of Emulsions/Microemulsions of the Salts

The controlled-release biocidal salts of the invention typically have limited solubility in aqueous media such as water. Therefore, for many of the applications described below, it is desirable to utilize the salts in the form of emulsions or microemulsions. The following is a generalized procedure for preparing emulsions or microemulsions of the salts.

First, the selected salt is dissolved in the minimum amount of a solvent that will completely dissolve the salt in the amount that is intended for use in the desired application. The solvent of choice will be one with the appropriate Hildebrand solubility parameter. The solubility parameter is a numerical value that indicates the relative solvency behavior of a specific solvent. Hildebrand solubility parameters of about 8.5 to about 22.0 are generally suitable for solubilization of the salts. Exemplary solvents with the requisite Hildebrand solubility parameters include ethanol, glycerin, propylene glycol, sorbitol, methanol and the like.

The desirable Hildebrand solubility parameter will depend on the ionic/covalent bonding energies of the salts. The correct solvent will be one having a relatively low Hildebrand solubility parameter if the bonding has more covalency and a relatively high Hildebrand solubility parameter if the bonding is more ionic. Of course, combinations of correct solvents may also be utilized to dissolve the salts.

Thereafter, a surfactant is added to the dissolved salt. The surfactant may be cationic, anionic or amphoteric in nature, and combinations of the different types or combinations of the same type of surfactants may be use. Preferably, the surfactant will be amphoteric or nonionic in nature. Highly negative anionic surfactants are not very functional.

The last step is to dilute the salt-solvent-surfactant composition with water to the concentration desired for the selected application so as to form an emulsion or microemulsion depending on the micellar size and the choice of solvents/cosolvents/surfactant(s).

The Surfactants

For the purposes of this invention, it is preferred that the surfactants employed in the formation of microemulsions (cosolvents are added) or emulsions of the salts are generally of the nonionic or amphoteric type or combinations of one or more nonionics, one or more amphoterics or one or more nonionics in combination with one or more amphoterics. Highly charged anionic surfactants are less desirable since they have the potential to reduce the biocidal activity of the salts by causing some degree of precipitation, thereby lessening the effectiveness of the salts.

It has also been found that cationic phospholipids, preferably in combination with nonionic and/or amphoteric surfactants are effective in the formation of microemulsions or emulsions of the salts.

Surfactants that carry a positive charge in strongly acidic media carry a negative charge in strongly basic media, and form zwitterionic species at intermediate pH levels are amphoteric. The preferred pH range for stability and effectiveness is about 5.0 to about 9.0. Within this pH range, the amphoteric surfactant is mostly or fully in the zwitter (neutral) form, thereby negating any dilution of biocidal activity of the salts, provided that the surfactant is employed in the preferred concentration range of about 0.25 to about 4.0 wt. %, based on the weight of the salt in the final formulation.

The following surfactants have been found to be effective in the formation of microemulsions or semi-transparent emulsions of the salts: amphoteric amidobetaines; nonionic polyethoxylated sorbital esters, polycondensates of ethylene oxide-propylene oxides (polyoxamers), polyethoxylated hydrogenated castor oils, and certain cationic phospholipids.

Suitable examples of amidobetaines include cocoamidoethyl betaine, cocoamido-propyl betaine; and mixtures thereof. Other suitable amphoteric surfactants include long chain imidazole derivatives such as the product marketed under the trade name "Miranol C2M" by Rhodia and long chain betaines such as the product marketed under the trade name "Empigen BB" by Huntsman Corporation, and mixtures thereof.

Suitable nonionic surfactants include polyethoxylated sorbitol esters, especially poly-ethoxylated sorbital monoesters, e.g., PEG sorbitan di-isostearate, and the products marketed under the trade name "Tween" by ICI; polycondensates of ethylene oxide and propylene oxide (polyoxamers), e.g., the products marketed under the trade name "Pluronic" by BASF; condensates of propylene glycol; polyethoxylated hydrogenated castor oil such as the products marketed under the trade name "Cremophors" by BASF; and sorbitan fatty esters marketed by ICI. Other effective nonionic surfactants include the polyalkyl ($C_8$-$C_{18}$) glucosides.

Suitable cationic surfactants include D,L-pyrrolidone-5-carboxylic acid salt of ethyl-cocoyl-L-arginate (CAE) marketed by Ajinomoto, and cocoamidopropyl (PTC), lauramidopropyl PG diammonium chloride phosphates and the like marketed by Uniqema.

APPLICATIONS

The controlled release biocidal salts of the invention are suitable for a wide range of applications. It should be understood that this list is presented for illustrative purposes only and does not represent any limitation as to possible applications. It should be further understood that it is within the purview of this invention that the products described below may be combined with conventional antioxidants, antibacterial agents, antifungal agents, hormones, vitamins, antioxidants, hydroxy acids, cleansers, soaps, shampoos, silicones, biocides, humectants, emollients, synthetic or natural oils, deodorizers, perfumes, colorants, preservatives, plant extracts, etc.

By way of summary, nonlimiting examples of such applications are as follows: a food or food product; a beverage; a preservative composition; a perishable item; a packaging; a plastic; a pharmaceutical product; a medical device, a cosmetic; a deodorant; a coating; a dental care composition; a dental care appliance; a dental hygiene product; a wound care composition; a dermatological care composition; a personal hygiene item; an infant care product; a surgical soap; a surgical or hospital gown; a microbiocide; an antifungal composition; an anti-yeast composition; an anti-mold composition; an animal care product; an apparel product; a woven or nonwoven or knit fabric; a foam; a film; a paper product; wood or a wood product; a construction material; plasterboard; a rubber item; and a virucide.

Additional applications of the controlled release biocidal salts of the invention are as follows:

(1) skin and hair care products, e.g., sunscreens; suntan lotions; after-sun gels, lotions and creams; antiperspirants; deodorants (solutions, powders, gels, roll-ons, sticks, sprays, pastes, creams, lotions); cleansing creams; skin conditioners; skin moisturizers; protectants; skin aging products; skin wrinkle reduction products; products for treatment of acne; products for treatment of rosacea; age-spot reduction products; stretch-mark reduction products; pimple treatment products, skin soothing products; skin infection and lesion treatment products; skin-redness reduction products; stretch-mark reduction products; varicose and spider-vein reduction products; lotions; oils; hand/body creams; shaving gels/creams; body washes; liquid and solid soaps; blood microcirculation improvement products, cellulite reduction products, body toning products, skin penetration enhancers; skin whitening products; cosmetics; shampoos; shower gels; bubble baths; hair treatment products, e.g., medicated shampoos, mousses, waxes, conditioners, styling agents, lotions, pomades, spray gels, hair dyes and tints, colorant and non-colorant rinses, detangling lotions, hair curling and hair straightening products, hair wave products, etc.; hand (or mechanical) dishwashing compositions; hand sanitizers; and disinfectants; lipsticks and lip balms; salves; collodion; impregnated patches and strips for skin treatment; skin surface implants; impregnated or coated diapers; and the like.

(2) dental care materials: mouthwash; dentifrice; dental floss coated and/or impregnated with the salt; protective coating for teeth; toothbrush bristles coated and/or impregnated with the salt; orthodontic appliance coated and/or impregnated with the salt; orthodontic appliance adhesive; denture appliance coated and/or impregnated with the salt; denture appliance adhesive; endo-dontic composition coated and/or impregnated with the salt; composite-type dental restorative materials; dental cement; dental liner; dental bonding agent; and the like.

(3) foods and food products: food-stuffs; animal feed-stuffs; grains; breads; bakery products; confectionary; potato products; pasta products; salads; soups; seasonings; condiments; syrups; jams, jellies and marmalades; dairy products; egg-based products; meats and meat-based products; poultry and poultry-based products; fish and fish-based products; crustaceans and crustacean-based products; fresh and dried fruit products; vegetables and vegetable products; greens; salads; sauces; beverages, e.g., wines, tea extracts, beers, juices; and the like.

(4) plastics and miscellaneous products, coated and/or impregnated with the salt, including: medical items, e.g., thermometers, catheters, surgical sutures, blood lines, implants, bandages, surgical dressings, surgical apparel, respirators, etc.; food packaging; fluid-dispensing tubing; drug and cosmetic packaging; eating utensils; shower curtains; bath mats; sponges; mops; toilet seats, rubber gloves; contact lenses; hearing aids; shelving paper; carpet pads; pool covers; animal bedding and cat litter; computer covers and computer keys; doorknobs;

tampons and sanitary napkins; adult novelties; sexual aids; sex toys; condoms; pregnancy barriers; dental chairs; dryer sheets; dishcloths; paints and coatings; powdered, liquid, gel and spray cleaners for floors, sinks, counter-tops, walls, tiles, carpets; deodorizing liquids, solids, sprays, gels and powders; filters; foams; hair brushes; combs; diaper rash preventer; plasma bag treatment; disposable glove treatment; additive to pasteurized cow milk; additive to blood sample tubes to inactivate HIV, HCMV, and other viruses (safety measure for lab technicians and healthcare providers); additives for condoms, band-aids, or bandages; additive for paint; or animal or plant treatment for microbial infections; and the like.

(5) fibers and fabrics coated and/or impregnated with the salt, including natural and synthetic fibers and fabrics manufactured from such fibers; wipes, cloths; surgical gauze; crib covers; bassinet covers; bed linens; towels and wash cloths; tents; draw sheets; cubicle curtains; shower curtains; wall coverings; wood and wood products; hospital clothing such as examination robes, physicians' coats, nurses uniforms, etc.; apparel; paper, non-woven fabric, knitted fabric, woven fabric, brick, stone, plastic, polymer, latex, metal, tile, walls, floors, gurneys, tables, or trays; shoes and the like.

Other potential applications are facial cream (as an acne treatment), bactericidal, fungicidal, virucidal; shampoo, hand lotion; athlete's foot medication (ointment, powder, soap); candies (for sore throat, bad breath, recurrent herpes); ointment or foam spray (for genital herpes legion treatment); shaving cream; mouth wash; after shave lotions; lip balm; paste; and the like In respect to food products, the controlled release biocidal salt of the invention will typically be applied to the food product in the form of an aqueous emulsion or microemulsion such that the salt will be present in an amount of about of about 10 to about 1,000 parts per million parts of food product, preferably 40 to 200 parts per million parts of food product. The salt may be applied to the food product by conventional techniques, e.g., spraying, immersion, dipping or injection.

Instead of, or in addition to, contacting the food product directly with the salt, the salt may be incorporated in a suitable packaging material by techniques such as dissolution in thermoplastic resins, melt spun or melt blown into the packaging material, etc. The packaging material may be any GRAS material, e.g. a thermoplastic material such as a polyolefin and copolymers thereof, polyesters, polyvinyl chloride, polyacrylate, polyamide, etc., that is suitable for packaging food products. The packaging material containing the salt of the invention would then be placed in contact with the food product. This technique would result in a wrapped perishable food and would greatly reduce the amount of preservative from finding its way into the food product.

The following nonlimiting examples shall serve to illustrate the embodiments of the invention. The examples are presented solely for the purpose of illustration and are not to be construed as limitation on the present invention since many variations are possible without departing from the spirit and the scope of the invention. Unless otherwise stated, all parts and percentages are on a weight basis.

EXAMPLE 1

Antimicrobial Activity of LAE Laurate 0.1 g of $N^\alpha$-lauroyl-L-arginine ethyl ester laurate (LAE laurate) was dissolved in 100 g of 1,2-pentanediol so as to provide a solution containing 1,000 parts per million of the salt. The solution was then applied to soya agar plates which had been previously inoculated with the bacteria indicated below and subsequently incubated at 37° C. for 48 hours. The results are set forth below in Table 1.

TABLE 1

Antimicrobial Activity of LAE Laurate

|  | Minimum Inhibitory Concentration, ppm |
|---|---|
| Gram Positive Bacteria |  |
| *Bacillus subtilus* | <25 |
| *Staphylococcus aureus* | <40 |
| Gram Negative Bacteria |  |
| *Enterobacter aerogenes* | <45 |

EXAMPLE 2

Antimicrobial Activity of Compounded Films

Two beef loins from a slaughterhouse were tested in a heat-sealed package simulating food packaging. The linear low density polyethylene film was compounded with 1% w/w LAE lactate biocidal salt of the invention. The results are reported in Table 2 below. The log colony forming units ("CFU") reduction values for bacteria that are part of the background flora of raw meat for both samples are 42 days indicate that there is a release of the salt of the invention from the polyethylene film to the surrounding beef surfaces.

TABLE 2

Antimicrobial Activity of Compounded Films

| Sample | Log CFU/g, days | | | | | Day 42 log reduction vs. control | Day 42 % reduction vs. control |
|---|---|---|---|---|---|---|---|
|  | 7 | 14 | 21 | 28 | 42 | | |
| control | 2.62 | 4.68 | 5.63 | 7.06 | 7.24 | 0 | 0 |
| LAE lactate | 2.31 | 3.68 | 3.97 | 5.32 | 5.57 | 1.67 | 97.9 |

EXAMPLE 3

Beef Purge Test

Two beef tenderloins containing a large quantity of purge (i.e., liquid surrounding raw meats; meat soaker pads were used to trap such liquids to the extent possible) were purchased at a local store. The purge was isolated from the packages and transferred to a series of test tubes and 10 ml of purge were placed in each test tube. To the test tubes was added 0.5 g of either LAE hydrochloride or LAE monolaurate salts. The samples were mixed in a vortex mixer and serial dilutions were then plated on petrifilm for readings at time zero. The test tubes were then placed in the refrigerator and were again plated at 24 hours and 48 hours. The beef purge contained naturally-occurring aerobic bacteria. The goal is to have >99% reduction of the bacteria after 48 hours. LAE hydrochloride was tested at 0.5 g/10 ml w/v. Both samples showed >99% reduction in bacterial counts after 48 hours. The results are reported in Table 3 set forth below. Note that the symbol "E" set forth in Table 3 is a scientific notation used to denote exponential values, e.g., the value noted as <1.000 E+2 is equivalent to <$1 \times 10^2$, the value noted as 3.89 E+04 is equivalent to $3.89 \times 10^4$, etc. Note that LAE-monolaurate contains about 66% of the active LAE cation.

TABLE 3

Beef Purge Test

| Sample | Avg. CFU/g 48 Hours | % Reduction |
|---|---|---|
| 5% w/w LAE-HCl | <1.000E+02 | 99.999 |
| 5% w/w LAE-Monolaurate | 2.82E+03 | 99.96 |
| Control | 7.08E+06 | — |

The results in Table 3 indicate that the salt of the invention, i.e., LAE mono-laurate performed as well as LAE-HCl after 48 hours, based on the test requirements.

EXAMPLE 4

Food-Grade Preservation Test

*Aloe vera* gel was prepared as a 50% dilution and dispensed as 20 g per container. Inoculum was prepared as 48 hour yeast cultures in tripticase soy broth and *A. niger* suspension. The inoculum was pooled and 100 μl added to each container. The preservatives were prepared as 1% solutions and added to each pre-labeled container. The samples were well mixed and stored. Recoveries were carried out at selected intervals (1:10 dilutions plated with sabourad dextrose agar. Pre-labeled plates were incubated at 25-30° C. for 48-72 hours; the pH of the samples was in the range of 4-4.5. The plates were removed from incubation, counted cfu recorded and converted to log reduction values.

As may be seen from Table 4 below, the initial challenge was 7 logs at day 0. Thereafter, re-challenges of 7 logs each were made at day 21 and day 28. The results were that after the two re-challenges, the LAE-lactate salt was superior to LAE-HCl. LAE-HCl showed a decrease at day 28 versus the LAE-lactate salt and almost no reduction at day 35 after the second re-challenge, compared to a 4.0 log reduction for the LAE-lactate salt. Further, the LAE-lactate salt continued to exhibit a log reduction even at day 42. These results clearly prove that the biocidal LAE-lactate salt of the invention possesses extended-release properties.

The preceding and following specific embodiments are illustrative of the invention. It is, however, to be understood that other expedients known to those skilled in the art or disclosed herein may be employed without departing from the spirit of the invention or the scope of the claims which follow after Table 4.

TABLE 4

| | Food-Grade Preservation Test | | | | | | | |
|---|---|---|---|---|---|---|---|---|
| | Day | | | | | | | |
| | 0 | 2 | 7 | 14 | 21 | 28 | 35 | 42 |
| Sample | Log Reduction Values | | | | | | | |
| LAE-HCl, 1725 ppm | 0 | 4.7 | 6.0 | 5.8 | 6.0 | 1.7 | 0.0 | 0.0 |
| LAE-lactate, 1500 ppm | 0 | 3.7 | 6.0 | 6.0 | 6.0 | 3.9 | 4.0 | 0.7 |
| Lactic acid, 1500 ppm | 0 | 1.0 | 0.2 | 0.0 | 0.0 | 0.0 | 0.0 | 0.0 |
| Control, 0 ppm | 0 | 0.6 | 0.2 | 0.0 | 0.0 | 0.0 | 0.0 | 0.0 |

What is claimed is:

1. A controlled release biocidal salt for application to skin or hair having a first component comprising the cation $N^{\alpha}$-lauroyl-L-arginine ethyl ester and a second component comprising an anion of carboxylic acid or of a carboxylic moiety of a saturated or unsaturated $C_8$-$C_{22}$ fatty acid, said salt being characterized such that when the salt is exposed to an aqueous medium, the salt partially dissolves thereby releasing from 2 ppm to 500 ppm biocidal ion, and further characterized as leaving a residual reservoir of undissolved salt capable of releasing more biocidal ions as the salt is consumed or otherwise removed from the environment encompassing the target bacteria, wherein all of the components of the biocidal salt are generally regarded as safe (GRAS) for food use or are found naturally in foodstuffs so that the biocidal salt could be ingested or applied to skin or hair with little or no side effects.

2. The salt of claim 1 wherein the carboxylate anion is selected from the group consisting of: adapalene, isotretinoin, pantothenic acid, benzoic acid, salicyclic acid, retinoic acid, tretinoin, aldobionic acid, undecylenic acid, an a-hydroxycarboxylic acid, a-hydroxycarboxy acid, an a-ketohydroxycarboxylic acid, a-ketohydroxycarboxy acid, an aromatic carboxylic acid, azelaic acid, glycolic acid, lactic acid, tartaric acid, mandelic acid, malic acid, citric acid, gluconic acid, glyceric acid, glyoxylic acid, myristic acid, palmitic acid, stearic acid, linolenic acid, arachidonic acid, oleic acid, linoleic acid, eicosapentanoic acid, docosahexenoic acid.

3. The salt of claim 1 which is formed by a metathesis reaction between a salt of $N^{\alpha}$-lauroyl-L-arginine ethyl ester and an anion.

4. The salt of claim 1 which is formed by the direct acid-base reaction between $N^{\alpha}$-lauroyl-L-arginine ethyl ester and an anion.

5. A product containing the salt of claim 1, said product being selected from the group consisting of a perishable item; a packaging; fluid-dispensing tubing; a plastic; a pharmaceutical product; a medical device, a cosmetic; a deodorant; a coating; a dental care composition; a dental care appliance; a dental hygiene product; a wound care composition; a dermatological care composition; a personal hygiene item; an adult novelty item; a sexual aid item; a sex toy item; a condom item; a pregnancy barrier item; an infant care product; a surgical soap; a surgical or hospital gown; a microbiocide; an antifungal composition; an anti-yeast composition; an anti-mold composition; an animal care product; an apparel product; a woven or nonwoven or knit fabric; a foam; a film; a paper product; a rubber item; and a virucide.

* * * * *